Figure 1:
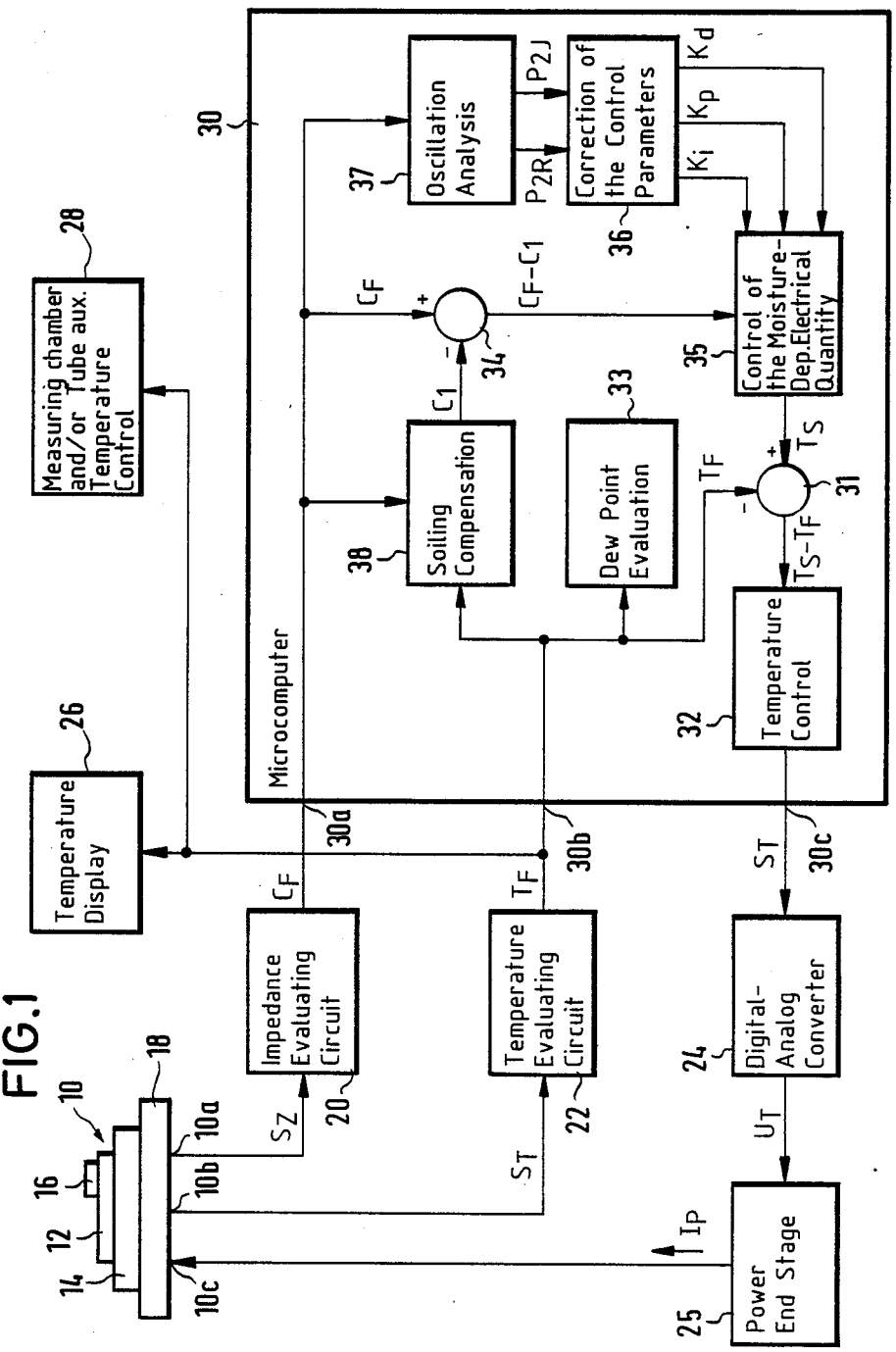

United States Patent [19]

Herrmann et al.

[11] Patent Number: 4,898,476

[45] Date of Patent: Feb. 6, 1990

[54] ARRANGEMENT FOR MEASURING THE WATER VAPOR DEW POINT IN GASES

[75] Inventors: Rainer Herrmann, Steinen; Dieter Funken, Lörrach, both of Fed. Rep. of Germany

[73] Assignee: Endress u. Hauser GmbH u. Co., Fed. Rep. of Germany

[21] Appl. No.: 236,667

[22] Filed: Aug. 25, 1988

[30] Foreign Application Priority Data

Dec. 1, 1987 [DE] Fed. Rep. of Germany ....... 3740719

[51] Int. Cl.$^4$ ............................................. G01N 25/68
[52] U.S. Cl. .................................... 374/28; 324/664; 364/557; 374/16
[58] Field of Search ............................ 374/16, 27, 28; 364/506, 557; 424/61 R

[56] References Cited

U.S. PATENT DOCUMENTS

| 3,284,003 | 11/1966 | Ciemochowski | 374/28 |
| 3,594,775 | 7/1971 | Fox | 364/557 |
| 3,873,927 | 3/1975 | Overall | 324/61 R |
| 4,174,498 | 11/1979 | Preikschat | 324/61 R |
| 4,378,168 | 3/1983 | Kuisma et al. | 374/28 |
| 4,383,770 | 5/1983 | Boschung et al. | 364/557 |
| 4,526,011 | 7/1985 | Logan et al. | 374/20 |
| 4,579,462 | 4/1986 | Rall et al. | 374/16 |
| 4,626,774 | 12/1986 | Regtien | 374/28 |

FOREIGN PATENT DOCUMENTS

| 0001919 | 5/1979 | European Pat. Off. | 324/61 R |
| 2640663 | 4/1977 | Fed. Rep. of Germany. | |
| 3231995 | 3/1984 | Fed. Rep. of Germany. | |
| 53-148485 | 12/1978 | Japan | 374/28 |
| 56-98644 | 8/1981 | Japan | 324/61 R |
| 58-165050 | 9/1983 | Japan | 374/28 |
| 61-237044 | 8/1986 | Japan | 324/61 R |
| 62-184342 | 8/1987 | Japan | 324/61 R |
| 62-217153 | 9/1987 | Japan | 324/61 R |
| 1307318 | 4/1987 | U.S.S.R. | 374/28 |
| 1548976 | 7/1979 | United Kingdom. | |
| 2028499 | 5/1980 | United Kingdom. | |
| 2126350 | 3/1984 | United Kingdom | 374/28 |

Primary Examiner—William A. Cuchlinski, Jr.
Assistant Examiner—Diego H. Gutieuez
Attorney, Agent, or Firm—Barnes & Thornburg

[57] ABSTRACT

For measuring the water vapor dew point in gases, a moisture-dependent electrical quantity of a sensor surface suitable for indicating formation of dew droplets is held by temperature control at a desired value corresponding to a stable dew mass. The temperature of the sensor surface corresponding to the desired value of the moisture-dependent electrical quantity is measured as dew point temperature. For compensating the influence of soiling, from time to time the desired value of the moisture-dependent electrical quantity is set in that the temperature of the sensor surface is lowered from a value lying above the dew point temperature and a periodic time temperature variation superimposed on the lowering. If the sensor surface is soiled, periodic time variations of the moisture-dependent electrical quantity occur at the same time but they become a monotonic variation when the dew point temperature is reached. The value of the moisture-dependent electrical quantity measured on the transition of the periodic time variations to a monotonic variation is then used as the reference or desired value which is maintained by the control of the temperature of the sensor surface. Furthermore, the control parameters for controlling the moisture-dependent electrical quantity are continuously corrected on the basis of an oscillation analysis.

16 Claims, 10 Drawing Sheets

FIG. 6
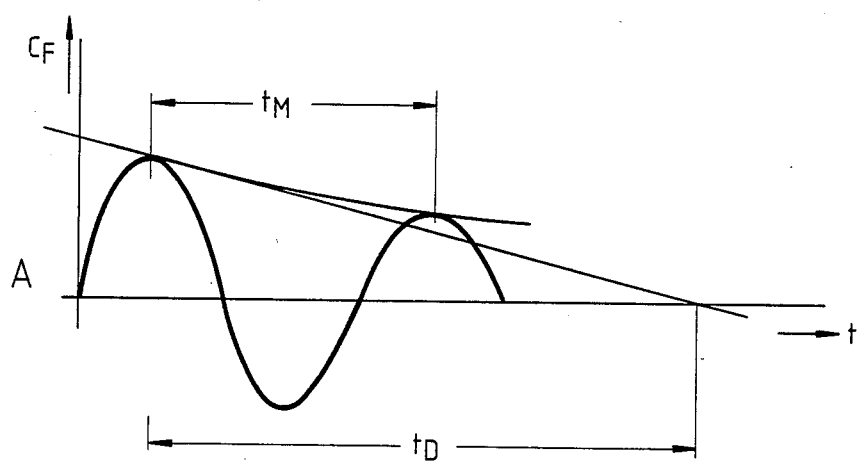
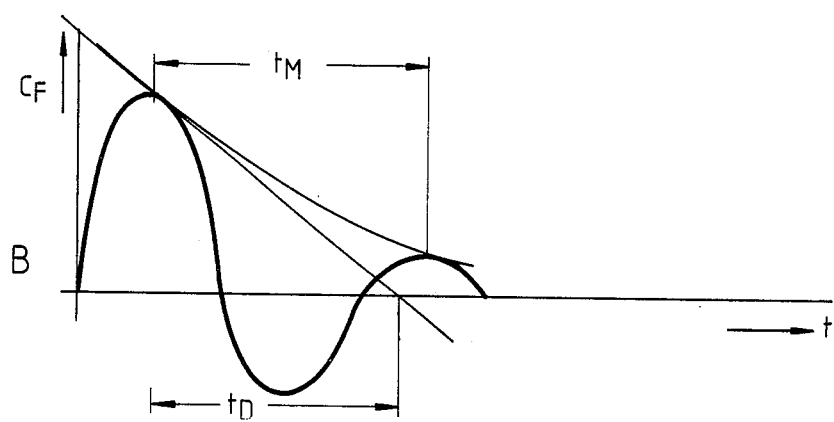
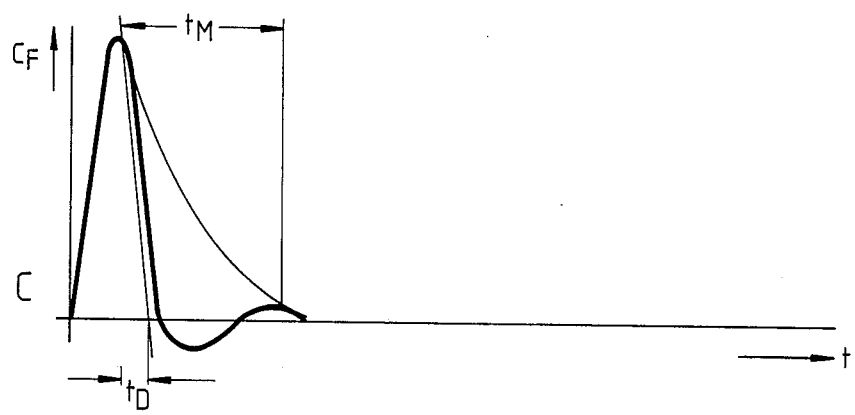

FIG.8
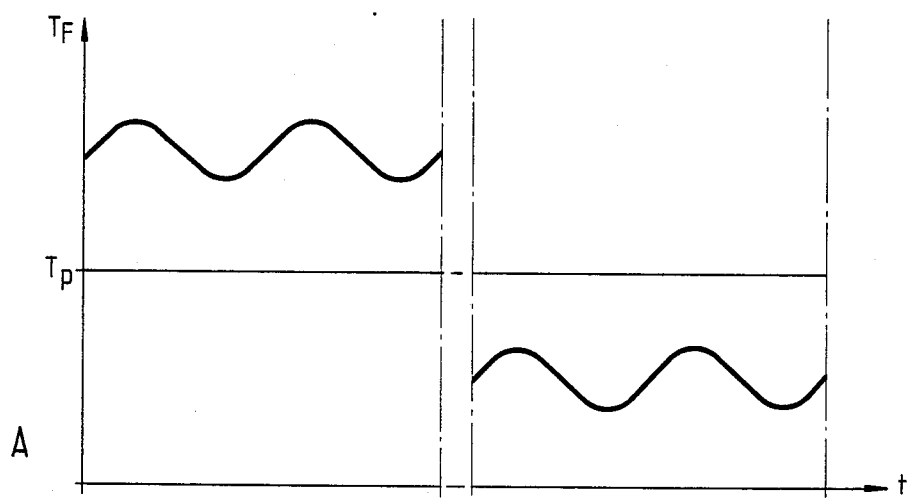
A
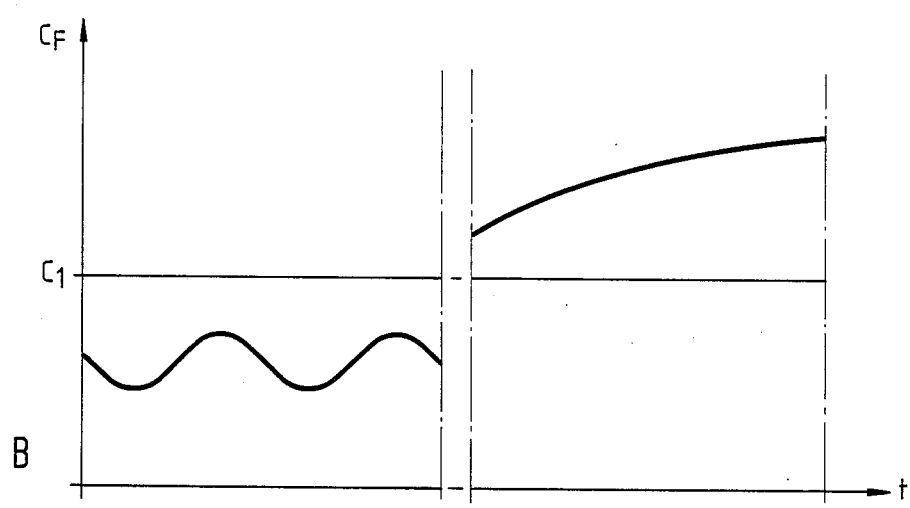
B

ARRANGEMENT FOR MEASURING THE WATER VAPOR DEW POINT IN GASES

The invention relates to a method for measuring the water vapour dew point in gases in which a moisture-dependent electrical quantity used for indicating the formation of dew droplets on a sensor surface is held, by controlling the temperature of the sensor surface, at a desired value associated with a stable dew mass and the temperature of the sensor surface is measured, and to an arrangement for carrying out the method.

Direct dew point measurement in this method is based on the fact that on the sensor surface water vapour condenses to dew droplets when the sensor surface is cooled to the dew point temperature and that the condensation is detectable from an associated value of the moisture-dependent electrical quantity; the temperature of the sensor surface measured at the start of the condensation is then the dew point temperature The dew droplets still remain of course when the temperature of the sensor surface is lowered beneath the dew point temperature, the mass of the condensate increasing as a function of time. For a continuous indication of the dew point temperature it is therefore necessary to keep the temperature of the sensor surface precisely at the value which corresponds to the start of the dew point condensation. This is the purpose of the temperature control.

The moisture-dependent electrical quantity used for the dew droplet detection is very often a capacitance but may also for example be an ohmic resistance or an impedance.

The correct determination of the dew point with this method requires the possibility of associating with the moisture-dependent electrical quantity unequivocably a value which it has at the dew point temperature. A desired value for the control of the moisture-dependent electrical quantity corresponds to said value. These conditions can be fulfilled for a given sensor without difficulty as long as the sensor is clean. However, the desired value determined and set for a given sensor is generally no longer valid when the sensor is soiled. Due to capillary condensation of the water vapour or the moisture solubility with oily soiling films, soiling of the sensor causes a change of the moisture-dependent electrical quantity even at temperatures which lie far above the dew point temperature and as a result the desired value corresponding to a clean sensor can be reached already at a temperature which is higher than the dew point temperature when the sensor surface is soiled. The temperature control then regulates the temperature of the sensor surface to this higher temperature and the latter is erroneously indicated as dew point temperature and evaluated. Soiling can therefore cause considerable measurement errors. To enable the dew point temperature to be correctly determined with a soiled sensor the value which the moisture-dependent electrical quantity of the soiled sensor has at the dew point would have to be known. This value changes however quite considerably in dependence upon the nature and degree of the soiling. It is known from German Pat. No. 3,231,995 to detect the soiling of a capacitive dew point sensor in that the phase angle of the sensor impedance present on dew formation is measured and used as a measure of the soiling. However, this step does not eliminate the measurement errors caused by the soiling; it only provides an indication that cleaning of the sensor is necessary or alternatively initiates an automatic cleaning operation when the measured soiling exceeds a predetermined limit value.

The problem underlying the invention is the provision of a method of the type set forth at the beginning in which the effects of soiling of the sensor surface are automatically compensated so that the dew point is correctly measured even with a soiled sensor surface irrespective of the nature and degree of the soiling.

According to the invention this is achieved in that, for setting the desired value, the temperature of the sensor surface is lowered from a value lying above the dew point temperature and a periodic time temperature variation is superimposed on the lowering and that on simultaneous occurrence of periodic time variations of the moisture-dependent electrical quantity the value of the moisture-dependent electrical quantity measured on the change of the periodic time variations to a monotonic variation is used as the desired value.

The invention is based on the recognition that soiling-induced variations of the moisture-dependent electrical quantity in the temperature range above the dew point temperature follow the temperature variations of the sensor surface whilst in the range beneath the dew point temperature. Each temperature, irrespective of whether it is rising or falling, causes a continuous increase in the mass of the condensed droplets and thus a monotonic variation of the moisture-dependent electrical quantity. With the aid of periodic time temperature variations superimposed on the temperature lowering it is therefore possible to clearly distinguish soiling-induced variations of the moisture-dependent electrical quantity from the variation caused by the condensation. The transition of the time profile of the moisture-dependent electrical quantity from periodic time changes to a monotonic change takes place at the dew point and the value of the moisture-dependent electrical quantity measured at said transition can be detected and evaluated as parameter for the soiling of the sensor surface. If this value is used as reference or desired value for the moisture-dependent electrical quantity the temperature of the sensor surface will be held correctly at the dew point.

Since the soiling of the sensor surface as a rule changes only slowly it suffices for the determination and setting of the desired value to be carried out at relatively large intervals of time.

A further advantageous development of the method for measuring the water vapour dew point in gases resides in that the control parameters for the control of the moisture-dependent electrical quantity are continuously corrected on the basis of an analysis of oscillations of the controlled variable of the moisture-dependent electrical quantity.

This further development makes it possible to cause the control of the moisture-dependent electrical quantity to run always in optimum manner With a control of the moisture-dependent electrical quantity having fixedly set control parameters it is not possible, without intervention from outside, to avoid instabilities or an unfavourable control behaviour throughout the entire range of the dew point temperatures to be detected. With the oscillation analysis according to the invention the control parameters can be continuously corrected in such a manner that instabilities detected can be eliminated and an optimum control behaviour obtained.

An arrangement for carrying out the method according to the invention includes a dew point sensor comprising an electrical sensor element which comprises the sensor surface and which furnishes an electrical signal dependent on the moisture-dependent electrical quantity, an electrical heating and cooling means influencing the temperature of the sensor surface, an electrical temperature sensor furnishing an electrical signal dependent on the temperature of the sensor surface, and a control arrangement which is connected to the dew point sensor and receives the moisture-dependent electrical quantity as a controlled variable and supplies to the electrical heating and cooling means a correcting variable by which the moisture-dependent electrical signal is held at a desired value, wherein the arrangement is characterized according to the invention in that the control arrangement includes a master controller and a follow-up controller which are arranged in cascade, that the master controller receives the moisture-dependent electrical signal as a controlled variable and the desired value of the moisture-dependent electrical signal as a command variable and emits a temperature desired value signal and that the follow-up controller receives the temperature desired value signal furnished by the master controller as a command variable and the temperature-dependent signal furnished by the temperature sensor as a controlled variable and supplies the correcting variable to the electrical heating and cooling means.

Advantageous further developments and embodiments of the method according to the invention and the arrangement for carrying out said method are characterized in the subsidiary claims.

Figure 2:
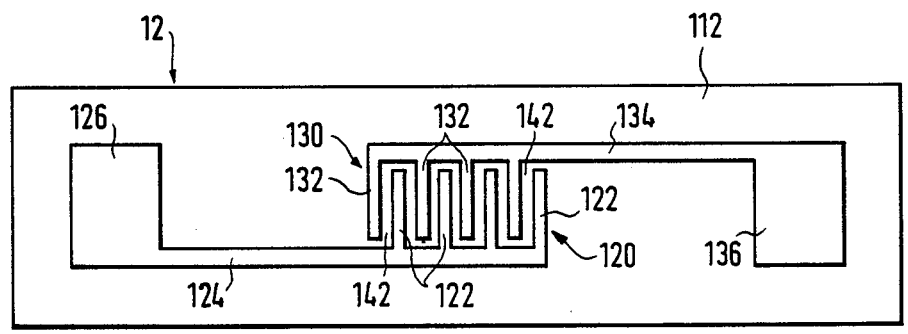
Figure 3:
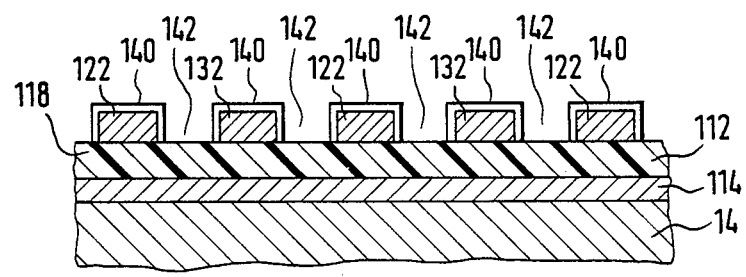
Figure 4:
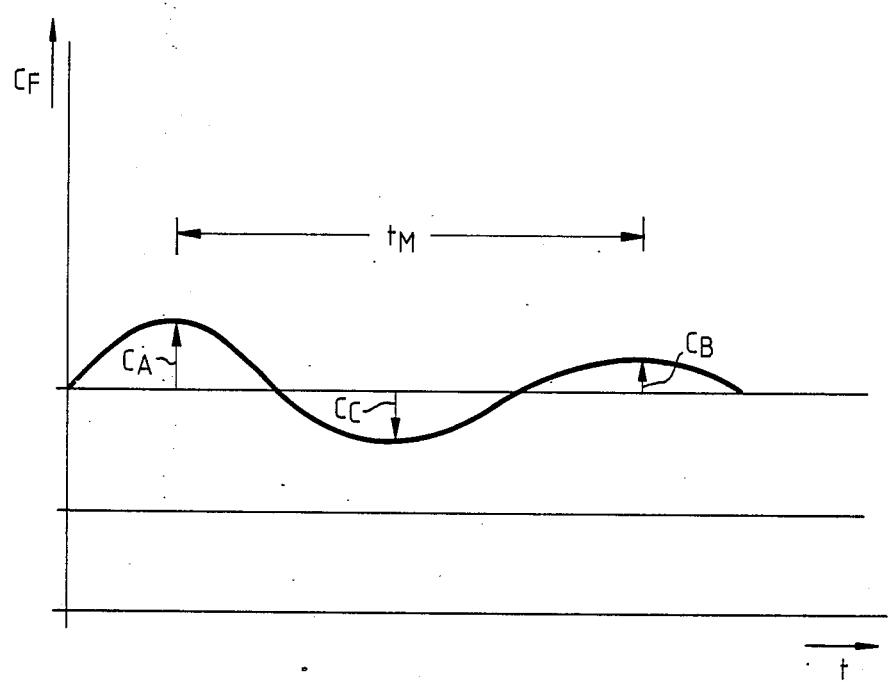
Figure 5:
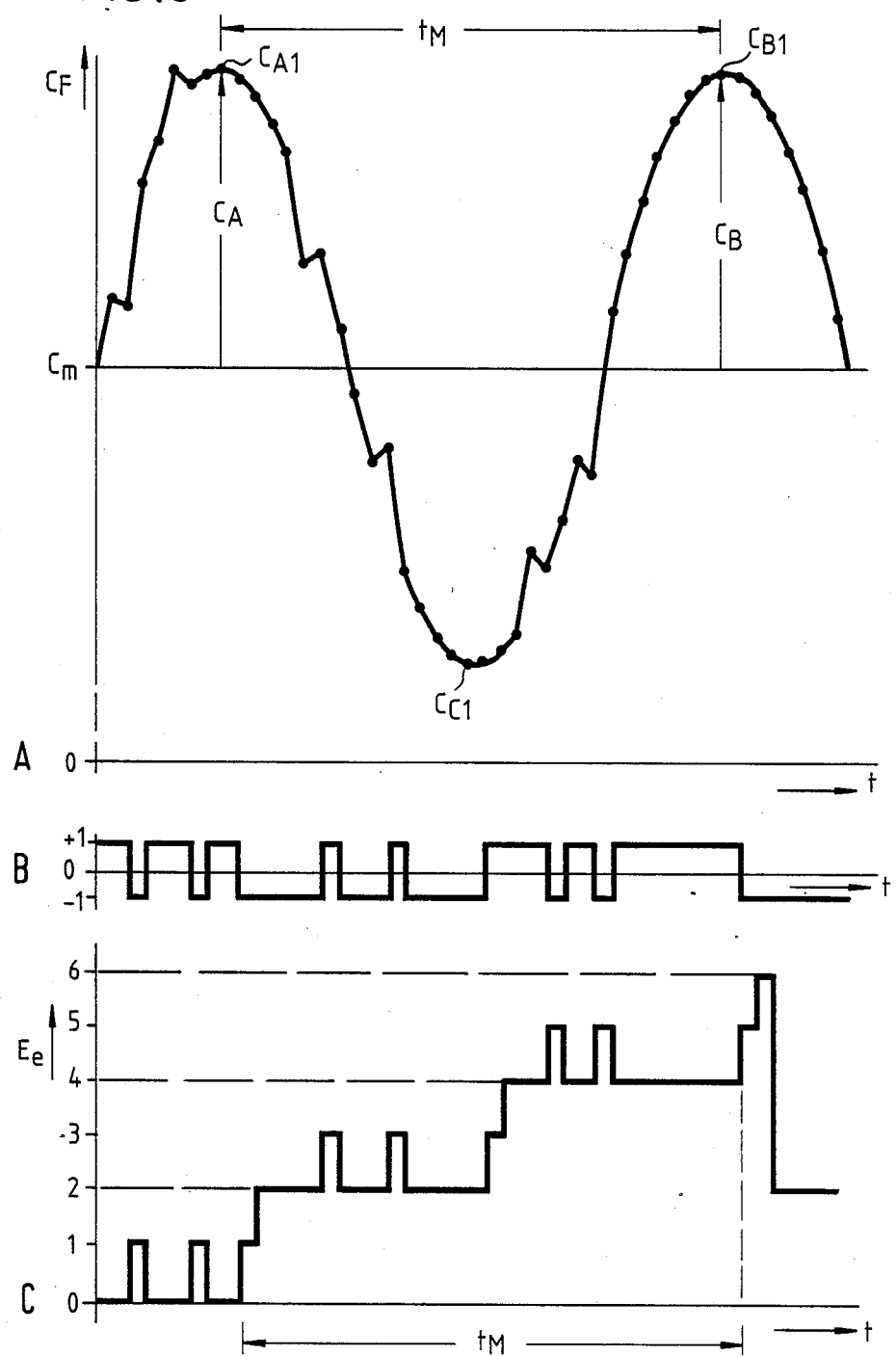
Figure 7:
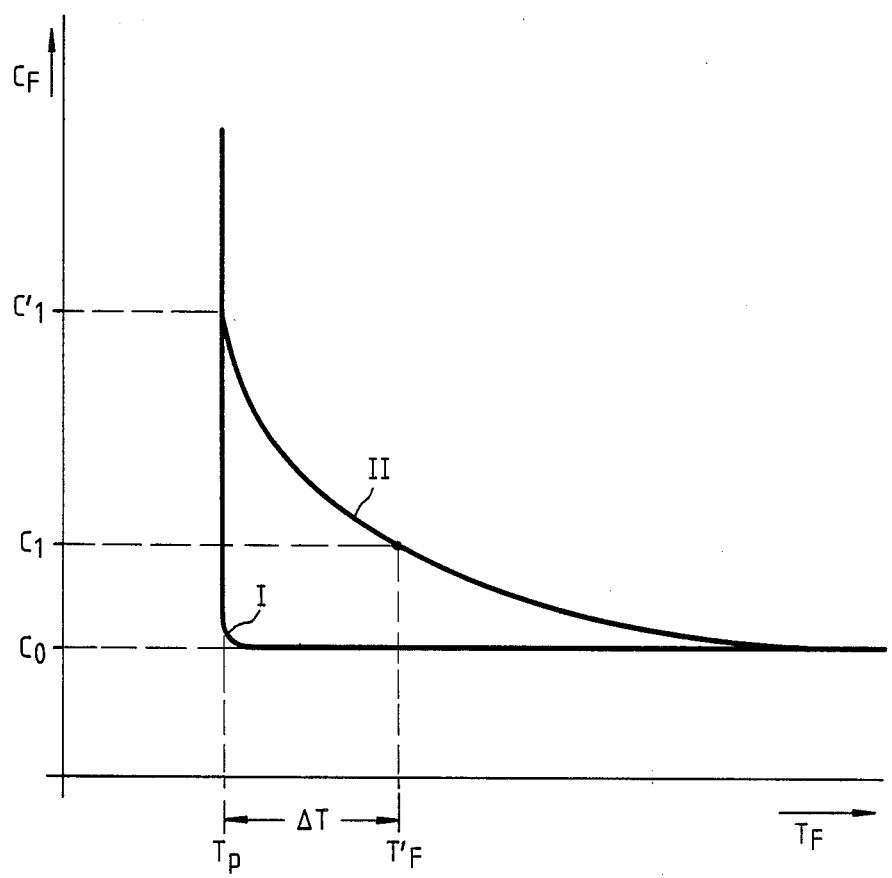
Figure 9:
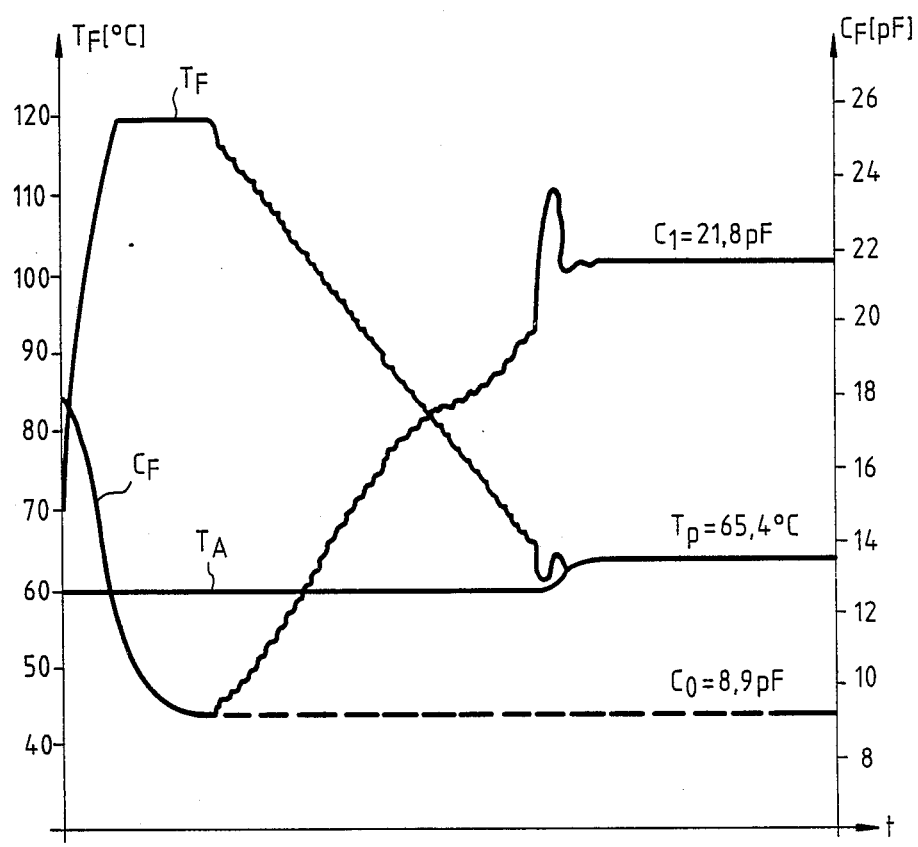
Figure 10:
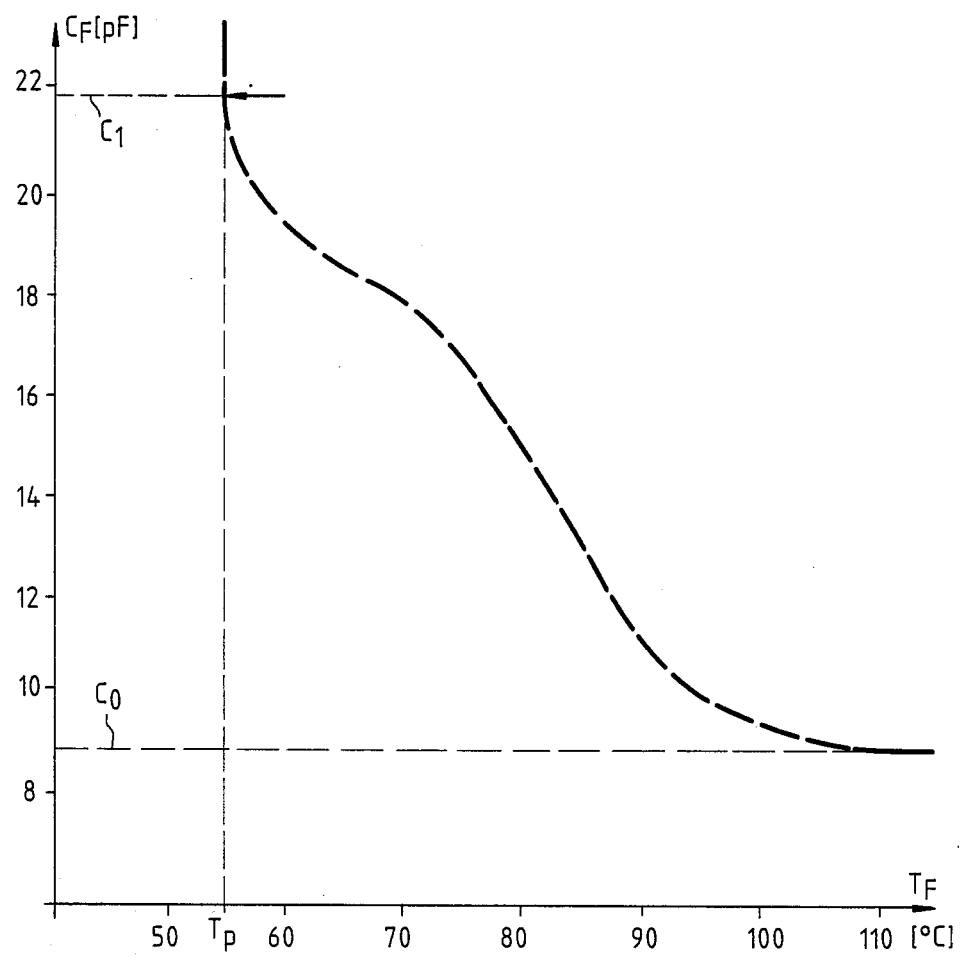
Figure 11:
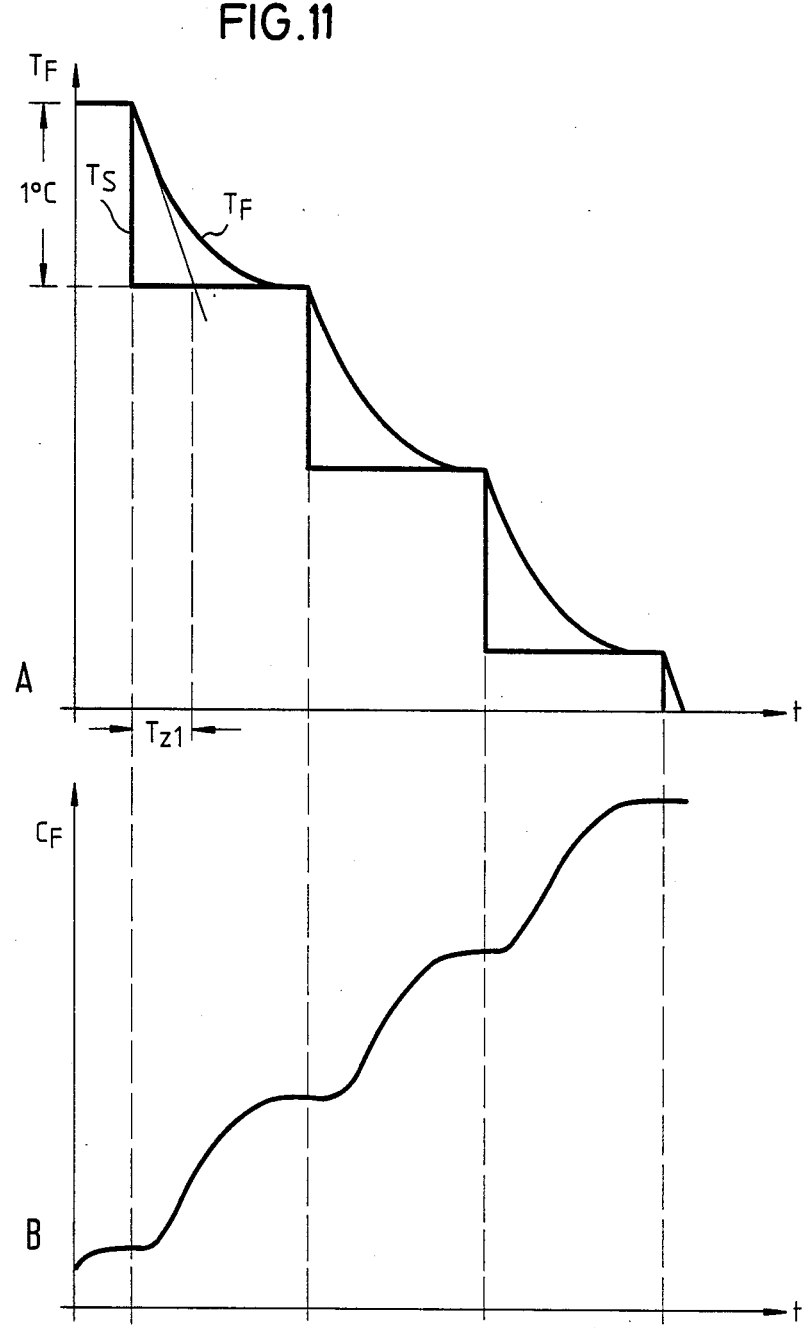

Further features and advantages of the invention will be apparent from the following description of an example of embodiment with the aid of the drawings, wherein:

FIG. 1 is the block circuit diagram of an arrangement for measuring the water vapour dew point in gases according to the invention, FIG. 2 is a plan view of a sensor element which can be used in the arrangement of FIG. 1, FIG. 3 is a section through part of the sensor element of FIG. 2 to a larger scale, FIG. 4 shows a possible time profile of the moisture-dependent electrical signal in the arrangement of FIG. 1, FIG. 5 shows diagrams to explain oscillation analysis which is carried out in the arrangement of FIG. 1, FIG. 6 shows diagrams of different oscillation forms of the moisture-dependent electrical signal which can occur in the arrangement of FIG. 1, FIG. 7 shows the relationship between the sensor capacitance and the sensor temperature with a clean dew point sensor and with a soiled dew point sensor, FIG. 8 shows diagrams to explain the principle which is employed when setting the desired value to obtain a soiling-independent temperature control in the arrangement of FIG. 1, FIG. 9 shows diagrams of the time profile of a cycle performed in the arrangement of FIG. 1 for soiling compensation, FIG. 10 shows the relationship derivable from the diagrams of FIG. 9 between the sensor capacitance and the sensor temperature with a soiled dew point sensor and FIG. 11 is a portion of the time profile of the cycle of the soiling compensation illustrated in FIG. 9.

The arrangement illustrated in FIG. 1 for direct measurement of the water vapour dew point in gases includes a measured value pickup 10 having an electrical sensor element 12 which is mounted on a Peltier element 14 serving as heating and cooling means, and a temperature sensor 16 responsive to the surface temperature of the sensor element 12. The Peltier element 14 is mounted on a support 18.

In the direct dew point measurement for determining the water content of a gas the non-ideal gas behaviour of water vapour is utilized, i.e. the capability of condensation due to intermolecular attraction forces when the gas is cooled at the surface of the sensor element 12 to a specific temperature which is the dew point temperature. The relationship between the water vapour partial pressure of the gas and the condensation temperature (dew point temperature) is represented by the saturation vapour pressure curve; this is the basis for the conversion of the direct measured quantity "dew point temperature" to all other moisture parameters.

To measure the dew point the surface of the sensor element 12 is exposed to the gas to be measured either by arranging the measured value pickup 10 directly in the process or by withdrawing gas from the process and introducing it into a measuring chamber in which the pickup 10 is arranged. With the aid of the Peltier element 14 the sensor element 12 is cooled until dew droplets form on its surface by condensation of water vapour. The occurrence of condensation is detected by means of the sensor element 12; the temperature measured simultaneously with the aid of the temperature sensor 16 is the dew point temperature. On further cooling of the sensor element 12 to still lower temperatures the magnitude of the dew droplets and thus the mass of the condensed water increases but the temperatures then measured are no longer decisive to the moisture parameters of the gas. Thus, the important point is to detect as accurately as possible the sensor temperature when the condensation starts. For a continuous dew point measurement the sensor temperature is kept, by temperature control, continuously at the value of the dew point temperature by maintaining a predetermined mass of the condensed water. The electronic circuits illustrated in FIG. 1 and connected to the measured value pickup 10 serve for the control of the moisture-dependent electrical quantity and the temperature control.

The electrical sensor element 12 must be designed so that it permits detection and control with the greatest possible accuracy both of the formation of the dew droplets on reaching the dew point temperature and of the maintaining of a predetermined mass of condensed water. For this purpose at least one electrical property of the sensor element must change in significant manner in dependence upon the formation of the mass of condensed water. Various types of electrical sensor elements are known which are wellsuited to a greater or lesser degree to this purpose. Very often the electrical property used to detect the formation of the condensate is the capacitance between two sensor electrodes which when the sensor electrodes are covered with condensate rises abruptly compared with the value in the dry state due to the higher dielectric constant of water. With other sensor elements the increase in the conductivity between two electrodes connected by the condensate is detected. Finally, it is also known to use the ohmic component and the capacitive component jointly to detect the compensation by measuring the impedance of the sensor element.

The sensor element described in copending U.S. patent application Ser. No. 204,628, filed Jun. 9, 1988 (corresponding to German patent application No. P 37 20 189.1-52 of June 16, 1987) is particularly well suited to the dew point measuring arrangement illustrated in FIG. 1. FIG. 2 shows a very simplified plan view of the sensor element 12 constructed in this manner and FIG. 3 shows a section through part of said sensor element 12 to a larger scale. Said sensor element 12 comprises a substrate 112 which consists of a moisture-insensitive insulating material. As apparent from FIG. 3 the substrate 112 is arranged on the Peltier element 14 with interposition of a separating layer 114 of aluminium. The free upper side of the substrate 112 remote from the separating layer forms the sensor surface 118 which is exposed to the gas of which the water vapour dew point is to be measured so that dew droplets form thereon due to condensation on cooling to the dew point temperature.

On the sensor surface 118 two electrode structures 120 and 130 are formed and are illustrated in FIG. 2 for clarity in very simplified manner. The electrode structure 120 has the form of a comb comprising a great number of parallel teeth 122 which are connected at one end to a web 124 extending perpendicularly thereto At the end of the web 124 a widened contact face 126 is integrally formed and serves for contacting a terminal conductor via which the electrode structure 120 is connected to the electronic circuit of the dew point meter. The electrode structure 130 comprises, in completely identical manner but in laterally inverted arrangement, teeth 122, a web 134 and a contact face 136. The teeth 122 and 132 of the two electrode structures lie in a small central region of the substrate 112 which forms the actual sensor region sensitive for the measuring operation. The teeth 122 and 132 are arranged alternately interengaging with each other, the teeth 122 of the electrode structure 120 lying in the intermediate spaces between the teeth 132 of the electrode structure 130 and conversely the teeth 132 of the electrode structure 130 lying in the intermediate spaces between the teeth 122 of the electrode structure 120. Thus, every pair of parallel adjacent teeth represents electrode portions belonging to different electrode structures. The intermediate spaces between the teeth of each electrode structure have a width such that in each intermediate space a tooth of the other electrode structure can be accommodated with adequate spacing from the two adjacent teeth. This is apparent in particular from FIG. 3 which shows to a greater scale than the illustration of FIG. 2 a section through several adjacent teeth 122, 132 of the two electrode structures 120 and 130 respectively.

Each tooth 122 and 132 of the two electrode structures 120, 130 is coated with a moisture-insensitive insulating layer 140 which completely covers all the free surfaces of the tooth. The teeth 122 and 132 are thus separated on the one hand by the insulating material of the substrate 112 and on the other by the insulating layer 140 completely from the gas of which the dew point is to be measured. In the embodiment illustrated in FIG. 3 there is a gap 142 extending up to the surface of the substrate 112 between the insulating layers covering the two adjacent teeth. The electrode structures 120 and 130 and the insulating layer 140 covering the teeth can be made on the substrate 112 by one of the usual methods known from thin-film technology and printed-circuit board technology. The electrode structures 120, 130 are formed for example by photolithographic technique from a suitable metal covering, for example tantalum or platinum. The insulating layer 140 must consist of a chemically stable electrically insulating and completely moisture-insensitive material. Possible for this are glass, resist or other suitable metal oxide. The material of the insulating layer can be applied to the electrode structures by any of the known methods. If the oxide of the metal used for the electrode structures 120, 130 has the necessary properties the insulating layer 140 can possibly be formed by surface oxidation of the conductor metal.

For clarification, in FIG. 2 the number of teeth in each electrode structure has been exaggeratedly reduced and the distance between the adjacent teeth shown exaggeratedly large. In reality each electrode structure 120, 130 has a very much greater number of teeth. A particularly important feature of this sensor element is the dimensioning of the spacing between adjacent teeth: it is less than 50 $\mu$m and is preferably about 20 $\mu$m. In a practically tested embodiment of a sensor element made by the principle of FIGS. 2 and 3 the electrode structures 120, 130 consist of tantalum which is applied to a substrate 112 of aluminium oxide. Each electrode structure comprises a comb of 50 teeth having a width of 21 $\mu$m and a length of 2 mm. The distance between the interengaging teeth of the two electrode structures is 19 $\mu$m. The actual sensor region formed by the two interengaging comb structures thus occupies an area of only 2×4 mm. The insulating layer 140 consists of highly compacted and thus moisture-insensitive tantalum oxide which is formed in a thickness of 160 nm by surface oxidation of the tantalum of the electrode structures.

The mode of operation of this sensor element is based on the fact that the distance between the adjacent teeth of the two electrode structures is of the order of magnitude of the greatest droplet forming when the dew point temperature is reached or is even smaller. As a result of this, the first condensation droplets forming when the dew point temperature is reached immediately fill the entire width of the gaps 142 between the adjacent teeth 122 and 132. As described in detail in U.S. patent application Ser. No. 204,628, filed June. 9, 1988 this results in an abrupt change in the impedance measured between the two electrode structures because the condensation droplets of relatively large conductivity short-circuit the relatively small capacitances of the gaps 142 and establish a conductive connection between the substantially greater capacitances of the insulating layers 140 covering the teeth. By measuring the impedance between the two electrode structures it is therefore possible to detect the reaching of the dew point temperature immediately on formation of the first condensation droplets even before a cohesive dew layer has formed.

Instead of the impedance the capacitance $C_F$ of the sensor element may also be measured. This changes from the dry capacitance value $C_O$ on reaching the dew point temperature to the substantially greater dew point capacitance value $C_1$. In the example of embodiment of the dew point measuring arrangement shown in FIG. 1 this measurement of the sensor capacitance $C_F$ is employed.

The measured value pickup 10 has a first terminal 10a at which an electrical signal $S_Z$ is available which depends on the moisture-dependent electrical quantity of the sensor element 12, thus on the impedance Z thereof when using the sensor element illustrated in FIGS. 2 and 3. Connected to the terminal 10a is an impedance evaluating circuit 20 which forms from the signal $S_Z$ an electrical signal which is suitable for the further processing and which represents the moisture-dependent electrical quantity used for the dew point detection, i.e. in the present case the sensor capacitance $C_F$. For simplification this signal is also denoted by $C_F$.

The measured value pickup 10 has a second terminal 10b at which an electrical signal $S_T$ is available which depends on the temperature-dependent electrical quantity of the temperature sensor 16. The temperature sensor 16 may for example be a thermoelement furnishing a temperature-dependent voltage or a resistance thermometer, the ohmic resistance of which varies with the temperature in the temperature range to be detected. In the example illustrated it is assumed that the temperature sensor 16 is a platinum resistance thermometer in thin-film technology of type PT 100. Consequently, the electrical signal $S_T$ available at the terminal 10b depends on the resistance of the temperature sensor 16. Connected to the terminal 10b is a temperature evaluating circuit 22 which forms from the signal $S_T$ an electrical signal which is suitable for the further processing and which represents the temperature $T_F$ of the surface of the sensor element 12 measured by the temperature sensor 16. For simplification this signal is also denoted by $T_F$.

The outputs of the impedance evaluating circuit 20 and the temperature evaluating circuit 22 are connected to two inputs 30a and 30b respectively of a microcomputer 30, and if necessary an analog-digital converter can be inserted in each case. In the microcomputer 30 the sensor temperature $T_F$ is compared with a desired temperature value $T_S$ calculated in the microcomputer as indicated by a comparison circuit symbol 31. The difference value $T_S - T_F$ obtained by the comparison is used in a function block 32, performing the function of a temperature controller, to generate a temperature control signal $S_T$ which is emitted at the output 30c of the microcomputer 30.

Of course, like the remaining function blocks illustrated the function block 32 is not physically present in the microcomputer 30; on the contrary, the function blocks represent different program routines of the microcomputer.

A digital-analog converter 24 connected to the output 30c of the microcomputer 30 converts the temperature control signal $S_T$ to a voltage $U_T$ which is applied to the input of a power end stage 25 which supplies the current $I_P$ for the Peltier element 14 to a third terminal 10c of the measured value pickup 10. This current $I_P$ is of course either a heating current or a cooling current, depending on its polarity. By the voltage $U_T$ applied to the power end stage 25 the Peltier current $I_P$ is set so that the difference $T_S - T_F$ becomes zero. By a known method the Peltier current $I_P$ can be periodically reversed in polarity for this purpose so that it acts alternately as heating current and cooling current, the voltage $U_T$ governing the duty cycle in such a manner that a mean sensor temperature $T_F$ arises which is equal to the desired or reference temperature $T_S$. The components 12, 16, 22, 31, 32, 24, 25, 14 thus form a temperature control circuit which continuously regulates the sensor temperature $T_F$ to the desired temperature $T_S$. In this temperature control circuit the sensor temperature $T_F$ is the controlled variable, the desired temperature $T_S$ the command variable and the Peltier current $I_P$ the correcting variable.

If it is ensured that the desired temperature $T_S$ is equal to the dew point temperature $T_P$ this temperature control keeps the sensor temperature $T_F$ continuously at the value of the dew point temperature $T_P$. In the regulated state a temperature display 26 connected to the output of the temperature evaluating circuit 22 then indicates the dew point temperature.

The microcomputer 30 may process in conventional manner the measured dew point temperature $T_P$, which is indicated by the signal $T_F$ in the regulated state, to obtain all the desired moisture quantities, as represented by a function block 33. For this purpose the saturation vapour pressure curve is stored as table in the microcomputer 30. This evaluation of the dew point temperature is generally known and will therefore not be further explained.

In the dew point measuring arrangement of FIG. 1 the microcomputer 30 in addition to its conventional functions is incorporated into the control of the moisture-dependent electrical quantity which regulates the sensor temperature $T_F$ to obtain a stable mass of the condensed water on the surface of the sensor element 12. For this purpose in the microcomputer 30 the sensor capacitance $C_F$ connected to the input 30a is compared with a capacitance desired value $C_1$ calculated in the microcomputer and associated with the dew point, as indicated by a further comparison circuit symbol 34. In a function block 35 fulfilling the function of a controller of the moisture-dependent electrical quantity, constructed as a proportional-plus-integral-plus derivative ("PID") controller, the difference value $C_F - C_1$ obtained by the comparison is employed to generate the desired temperature value $T_S$ which is used for the comparison in the symbolically illustrated comparison circuit 31. The desired temperature $T_S$ is set by the control in the function block 35 in such a manner that the difference $C_F - C_1$ becomes zero, i.e. the sensor capacitance $C_F$ assumes the dew point capacitance desired value $C_1$. Assuming that the capacitance desired value $C_1$ corresponds to the sensor capacitance at the true dew point temperature, in this manner the sensor temperature $T_F$ is obtained by regulation to the dew point temperature $T_P$. By displaying the temperature represented by the temperature signal $T_F$ in a temperature display 26, in the regulated stabilized state the dew point temperature $T_P$ is indicated.

A second control circuit is thus present which runs from the sensor element 12 over the impedance evaluating circuit 20 and the function blocks 34, 35 of the microcomputer 30 to the temperature control circuit. In the second control circuit the sensor capacitance $C_F$ is the controlled variable and the dew point capacitance desired value $C_1$ the command variable. The correcting variable $T_S$ of the second control circuit forms at the same time the command variable of the temperature control circuit. This is thus a cascade control, the outer second control circuit containing the inner temperature control circuit. The controller of the moisture-dependent electrical quantity of the outer control circuit represented by the function block 35 acts as master controller and the temperature controller 32 of the inner control circuit acts as follow-up controller.

The inner control results in the surface temperature $T_F$ of the sensor element 12 following within the shortest possible time the desired temperature value $T_S$ prescribed by the controller 35. The control parameters of the temperature controller 26 remain constant in the entire temperature range even under extremely varied use conditions. An essential requisite for this inner temperature control is that it takes place faster than the outer control.

The actual dew point determination is made by the outer control controlling the capacitance $C_F$ (or generally the moisture-dependent electrical quantity used) of the measured value pickup 10 by the variation of the sensor temperature $T_F$.

If the pickup 10 is not directly arranged in the process but in a measuring chamber into which gas withdrawn from the process is introduced the actual sensor temperature $T_F$ serves as desired or reference value for a parallel control of the measuring chamber temperature as represented by the circuit block 28. This control is effected in such a manner that the measuring chamber temperature is held a predetermined amount above the sensor temperature; said amount may be different for various temperature ranges of the sensor temperature. Parallel to the temperature of the measuring chamber the measuring chamber temperature control also controls the temperature of the tube auxiliary heating.

With the aid of the cascade control described the properties of the substantially simpler temperature control are utilized for simplifying the control of the moisture-dependent electrical quantity:

(a) Disturbances due to gas temperature changes have no influence on the control of the moisture-dependent electrical quantity because they are taken up by the separate internal temperature control.

(b) The feedback within the control of the moisture-dependent electrical quantity due to variation of the energy balance at the sensor surface because of water vapour condensation (or evaporation) is equalized by the separate internal temperature control because variations in the energy balance are regulated out by the separate temperature controller.

The incorporation of the microcomputer 30 into the control circuits permits an automatic influencing of the control for eliminating interfering influences and for obtaining an optimum control behaviour. To this end, the microcomputer 30 fulfils in particular the following functions:

1. The system itself optimizes the control parameters of the PID controler 35 in accordance with the dynamics of the controlled member.
2. The desired value for the value of the moisture-dependent electrical quantity of the sensor 10 corresponding to the dew point, i.e. the value $C_1$ of the sensor capacitance $C_F$ in the example described, is automatically determined by the system in a manner such that soiling of the sensor which could lead to erroneous measurement is compensated.
3. In the soiling compensation cycle the time constant $T_{z1}$ of the follow-up controller 32 is simultaneously intended for the control of the temperature of the Peltier element 14; for this purpose the microcomputer 30 is incorporated into the temperature control circuit.

These functions will be explained below.

Self-optimizing of the dew point control

In the normal state of the control, in time constant cycles having a cycle time $\Delta t_x$ of about 0.5 to 1 s in each case the PID controller represented by the function block 35 defines a new temperature desired value $T_S$ which differs from the preceding desired value $T'_S$ by a desired value change $\Delta T_S$:

$$T_S = T'_S + \Delta T_S \quad (1)$$

The following equation applies for the desired value change $\Delta T_S$ per cycle $$\Delta T_S = K_i (C_F - C_1) \Delta t_x + K_p \cdot \Delta (C_F - C_1) + K_d \cdot \Delta^2 (C_F - C_1) / \Delta t_x \quad (2)$$

In this equation $K_i$, $K_p$, $K_d$ are the control parameters for the integral, proportional and differential control respectively of the PID controller of the function block 35. The peculiarity of the measuring arrangement illustrated resides in that the control parameters $K_i$, $K_p$, $K_d$ are not fixedly set but can be changed by the system in dependence upon the time behaviour of the controlled member.

A correction of the control parameters is carried out whenever the desired value correction $\Delta T_S$ determined in a cycle $\Delta t_x$ is too great and the system therefore starts to oscillate or when it is so small that the condensation or evaporation processes no longer keep up with the moisture variation in the gas.

The correction of the control parameters is effected by a program routine which is represented in FIG. 1 by a function block 36 on the basis of the result of an oscillation analysis of the control circuit represented by the function block 37. FIG. 4 shows as example a decaying oscillation of the sensor capacitance $C_F$ about the desired value $C_1$. The oscillation has the oscillation period $t_M$ and two consecutive positive amplitudes $C_A$, $C_B$ between which a negative amplitude $C_C$ lies. From the values $t_M$, $C_A$ and $C_B$ the real component $P_{2R}$ and the imaginary component $P_{2J}$ of the pole of the transfer function of the dew point control can be calculated by the following equations:

$$P_{2R} = -\frac{\ln(C_A/C_B)}{t_M} \text{ (oscillation decrement)} \quad (3)$$

$$P_{2J} = \frac{2\pi}{t_M} \text{ (oscillation circuit frequency)} \quad (4)$$

These relationships hold true irrespective of whether the oscillation $C_F$ is decaying, whether it happens to be building up or whether it is present with constant amplitude.

The oscillation analysis represented by the function block 37 is called up both in the entry process on each starting up of the apparatus and in the normal control process in each $\Delta t_x$ cycle. As a result of the oscillation analysis the function block 37 supplies the values of the two oscillation parameters $P_{2R}$ and $P_{2J}$ to the function block 36.

Instead of the oscillation of the sensor capacitance $C_F$ in the outer control circuit it is equally possible to utilize for the oscillation analysis the oscillation of the sensor temperature $T_F$ in the internal control circuit. The following description applies accordingly to that case as well.

The problem exists of correctly detecting from the digital sampled values of the sensor capacitance $C_F$ or the sensor temperature $T_F$ the maxima and minima of the oscillation curve to enable random fluctuations to be distinguished from genuine oscillations and long-time oscillations to be detected as well. To solve this problem the oscillation analysis is carried out in the function block 37 by a "three-differential method" which will be explained with the aid of the diagrams of FIG. 5.

Diagram A of FIG. 5 shows consecutive digital sampled values which are derived from the analog curve representing the sensor capacitance $C_F$ as a function of the time. The sampled values are connected by straight lines, thereby approximately simulating the analog curve. The oscillation runs approximately sinusoidally about a mean value $C_m$.

In diagram B the sign of the slope of the curve portions between the consecutive sampled values is represented and is also the sign of the differential of the corresponding portions of the analog curve. The value $+1$ corresponds to the positive sign, i.e. a rising curve portion, and the value $-1$ corresponds to the negative sign, i.e. a declining curve portion. The sign for each curve portion cannot be determined until the second sampled value is available; consequently, a sign change applying to the preceding curve portion coincides in diagram B in time with the second sampled value of said curve portion in diagram A.

The first sampled value of diagram A lies in the origin of the coordinate system. It is assumed in diagram B that the slope of the preceding curve portion (not illustrated in diagram A) had a positive sign. This positive sign corresponds in diagram B to the value $+1$ which is held until the second sampled value is available. At the instant of the second sampled value it is found that the slope of the curve portion between the first and second sampled values also had a positive sign. For this reason in diagram B between the second and third sampled values the value $+1$ is further held although the curve portion between said two sampled values declines, i.e. has a negative slope.

The negative slope of the preceding curve portion can only be determined when the third sampled value is available. For this reason the sign curve of diagram B changes at the instant of the third sampled value to the value $-1$ which is now held until the fourth sampled value is present although the slope between the third and fourth sampled value is again positive. The new sign change is not detected until the instant of the fourth sampled value so that at said instant the curve of diagram B again goes from the value $-1$ to the value $+1$. The further formation of the sign curve of diagram B from the sampled values of diagram A will be readily understood on the basis of the above explanation.

A permanent sign change of the slope of the oscillation curve indicates an extreme value (minimum or maximum). Such a permanent sign change must be distinguished from sporadic sign changes occurring due to brief disturbances in the curve profile. Thus, in diagram A between the first and second curve portion a sign change is apparent which is however cancelled again by another sign change between the second and third curve portions. To prevent such sporadic sign changes being erroneously interpreted as extreme values, in the microcomputer 30 a count variable $E_e$ is set in dependence upon the sign changes of diagram B in the manner illustrated in diagram C.

On each sign change of diagram B which could correspond to an extreme value the count variable $E_e$ is incremented by "1". However, on an immediately following sign change it is decremented again by "1". If on the other hand the sign change indicating an extreme value is not followed in the next curve portion by another sign change the extreme value is confirmed by the count value $E_e$ again being incremented by "1".

It is apparent from diagram C that the first maximum is reached when the count variable has reached the value $E_e=2$. The sampled value $C_{A1}$ corresponding to the preceding sign change is now held and from the instant of this sign change onward the time is counted for measuring the oscillation period.

The minimum of the oscillation is reached for $E_e=4$ and the second maximum is reached for $E_e=6$. On the sign change corresponding to this second maximum the associated sampled value $C_{B1}$ is held and the time measurement terminated. The measured time is the oscillation period $t_M$. The oscillation amplitudes of the two maxima are derived from the sampled values:

$$C_A = C_{A1} - C_m \quad (5)$$

$$C_B = C_{B1} - C_m \quad (6)$$

If $C_{C1}$ is the sampled value value at the minimum of the oscilation then the mean value of the oscillation is given as $$C_m = \frac{C_{A1} \cdot C_{B1} - C_{C1}^2}{C_{A1} + C_{B1} - 2C_{C1}} \quad (7)$$

Thus, all the values necessary for calculating the oscillation parameters $P_{2R}$ and $P_{2J}$ are available.

As a rule the second maximum is used again as starting point for a new oscillation measurement. The count variable is therefore not reset to "0" but to $E_e=2$.

The next step is to assess whether the oscillation analyzed in this manner is suitable for self-optimizing of the control. For example, a detected "oscillation" is considered unsuitable for self-optimization if the oscillation amplitudes detected are too small compared with the oscillation mean value $C_m$. Furthermore, the oscillation parameters $P_{2R}$ and $P_{2J}$ calculated from the measured quantities $C_A$, $C_B$, $t_M$ must fulfil the criteria of an oscillation. The attenuation time constant $t_D$ governing the exponential time decay of the oscillation curve must not be appreciably shorter than the measured oscillation period $t_M$. This condition is represented in the diagrams of FIG. 6: in diagram A the oscillation time constant $t_D$ is greater than the measured oscillation period $t_M$ and in diagram B it is only slightly smaller; these two oscillations can be allowed for correction of the control parameters. In contrast, in diagram C the attenuation time constant $t_D$ is very small compared with the measured oscillation period $t_M$; this oscillation is therefore not allowed.

When all the requirements for correction of the control parameters $K_i$, $K_p$, $K_d$ are fulfilled on the basis of the oscillation analysis made the program routine represented by the function block 36 calculates the new control parameters in the following manner:

If
$T_{z1}$ is the time constant of the temperature controller 32 measured in the soiling cycle,
$T_{z2}$ is the time constant of the thermal delay of the sensor element 12 calculated from the oscillation analysis and
$T_r$ is the time constant of the control of the moisture-dependent electrical quantity in the exponential aperiodic limit case,
then for the new control parameters of the aperiodic limit case associated with the three constants we have:

$$K_d = X \cdot \left( \frac{3}{T_r^2} - Y \right) \qquad (8)$$

$$K_p = X \cdot \frac{1}{T_r^3} \qquad (9)$$

$$K_i = \frac{K_p}{K_d + XY} K_p \qquad (10)$$

The parameters X, Y and $T_r$ are to be calculated from the old control parameters $K_p'$, $K_i'$, $K_d'$ and from the oscillation parameters $P_{2R}$, $P_{2J}$ obtained by the oscillation analysis in accordance with the following equations:

$$X = \frac{K_p'}{(P_{2R}^2 + P_{2J}^2)\left( 2 P_{2R} + \frac{3}{T_R} \right)} \qquad (11)$$

$$Y = \frac{1}{T_{z1}} \cdot \frac{1}{T_{z2}} \qquad (12)$$

$$\frac{1}{T_r} = \left( \frac{1}{T_{z1}} + \frac{1}{T_{z2}} \right) \cdot \frac{1}{3} \qquad (13)$$

where $$\frac{1}{T_{z2}} = \frac{K_p'}{K_d'} \qquad (14)$$

$$\frac{P_{2R}^2 + P_{2J}^2 - \left[ (P_{2R}^2 + P_{2J}^2)\frac{K_d'}{K_p'} + 2 P_{2R} \right]\left( 2 P_{2R} + \frac{1}{T_{z1}} \right)}{P_{2R}^2 + P_{2J}^2 + \frac{K_p'}{K_d'} \cdot \left( 2 P_{2R} + \frac{1}{T_{z1}} \right)}$$

The theory of self-optimization of the dew point control requires that the following must apply for the calculated values of $T_{z2}$ and Y $$T_{z2} > 0$$

$$Y > 0,$$

for the value for Y according to the theory is a very small positive correction value for calculating $K_d$ in accordance with equation (8).

As shown by the equations (8), (9) and (10) there exists a typical set of control parameters $K_p$, $K_i$, $K_d$ for each given value of the time constant $T_r$ of the ideal transient process in the aperiodic limit case.

The limited performance of the Peltier element also requires limitation of the differential component of the dew point control. The differential component is decisive for rapid response of the dew point controller to a disturbance. In fact, the self-optimizing described always furnishes a differential component which substantially exceeds the other quantities. In order to take account of the limited cooling power of the Peltier element the following limit value for $K_d$ should be observed:

$$K_d < 10 \cdot K_p.$$

Soiling compensation

FIG. 7 shows the influence of a soiling of the measured value pickup 10 on the relationship between the sensor capacitance $C_F$ and the sensor temperature $T_F$.

The curve I corresponds to the clean sensor. It shows that when the sensor temperature is lowered the sensor capacitance $C_F$ corresponds to the dry capacitance $C_0$ until the dew point temperature $T_P$ is almost reached. Just before the dew point temperature $T_P$ is reached the sensor capacitance rises slightly and then increases exactly at the dew point temperature $T_P$ to a value which is very much greater than the dry capacitance $C_0$. The dew point sensor is thus substantially correctly held at the dew point temperature $T_P$ if the sensor temperature $T_F$ is regulated so that the sensor capacitance assumes the value $C_1$ illustrated.

The curve II corresponds to a soiled sensor. On lowering of the sensor temperature $T_F$ the sensor capacitance $C_F$ rises due to capillary condensation of water vapour or moisture solubility of the oily soiling films even though the sensor temperature is still far above the dew point. Depending on the nature of the soiling this rise of the sensor capacitance $C_F$ can even start at temperatures lying up to 100° above the dew point.

Now, if the sensor capacitance $C_F$ is held by the temperature control at the same value $C_1$ as with the clean sensor the sensor temperature $T_F$ will not correspond to the dew point $T_P$ but to a higher value $T'_F$. The result is a measuring error $\Delta T$ in the measurement of the dew point temperature. To ensure that the dew point sensor is held at the correct dew point temperature $T_P$ the control would have to be such that the sensor capacitance $C_F$ is held by the temperature control at the value $C'_1$.

The value $C'_1$ applies of course only for the nature and degree of the soiling which give the curve II. Other types and/or degrees of soiling each give different values of the sensor capacitance $C_F$ at the dew point $T_P$.

In the measuring arrangement of FIG. 1 in the microcomputer 30 a program routine represented by the function block 38 automatically sets the capacitance value $C_1$ used as command variable for the temperature control so that it corresponds exactly to the sensor capacitance $C_F = C'_1$ at the dew point $T_P$. In this manner the previously explained effects of soiling of the sensor are automatically compensated.

For this purpose a method is used which makes it possible to distinguish the soiling-induced variations of the measurement signal $C_F$ above the dew point temperature from the variations caused by the surface condensation of the water vapour at and beneath the dew point temperature.

The principle underlying this method will now be explained with the aid of the diagrams of FIG. 8. Diagram A of FIG. 8 represents the sensor temperature $T_F$ as a function of the time. In the left part of the diagram A it is assumed that the sensor temperature $T_F$ is periodically varied in the range above the dew point temperature $T_P$. For the sake of a simpler illustration it will be assumed that a sinusoidal variation is involved. These variations take place of course relatively slowly due to the thermal inertia of the dew point sensor. Furthermore, the amplitude of the variations has been exaggerated for clarification.

In the right part of diagram A corresponding variations of the sensor temperature $T_F$ are represented in the range beneath the dew point temperature $T_P$.

Diagram B shows how the sensor capacitance $C_F$ of a soiled sensor varies as a function of the time t for the temperature variations according to diagram A. In the range above the dew point temperature the relationship between the temperature variations and the capacitance variations are shown by curve II of FIG. 7. In this range the capacitance of the soiled sensor changes oppositely to the sensor temperature in accordance with the profile of the capacitance-temperature characteristic defined by curve II. These capacitance variations lie in the range between the dry capacitance $C_0$ and the dew point capacitance $C'_1$ of the soiled sensor.

In contrast, the capacitance of a clean sensor would not change in this range, as apparent directly from FIG. 7, because the capacitance temperature characteristic represented by curve I for the clean sensor runs horizontally in this range. On temperature variations, the clean sensor retains in this range the dry capacitance value $C_0$ unchanged.

In the range beneath the dew point temperature however the capacitance of the soiled sensor no longer follows the variations of the sensor temperature as represented in the right part of the diagrams. In this range the capacitance of the soiled sensor is governed by the dew condensation forming on the surface of the sensor element. Any further soiling-induced condensation ceases. The mass of condensed water increases continuously at any temperature lying sufficiently beneath the dew point. Consequently, in this range a continuous increase of the sensor capacitance $C_F$ takes place even if the sensor temperature varies.

In the dew point measuring arrangement illustrated in FIG. 1 this different behaviour of a soiled sensor at temperatures beneath and above the dew point temperature is utilized for determining the sensor capacitance $C_1$ corresponding to the dew point.

FIG. 9 shows a soiling compensation cycle as carried out in particular on each starting up of the apparatus for determining the dew point capacitance value $C_1$. This cycle also gives the dry capacitance $C_0$ of the sensor as well as the time constant $T_{z1}$ of the follow-up controller.

The diagram of FIG. 9 shows the profile of the sensor temperature $T_F$ compelled by the system and the resulting time profile of the sensor capacitance $C_F$ of a sensor completely soiled with an oily film during the soiling compensation cycle. With a sensor soiled in this manner the sensor capacitance $C_F$ rises already at a temperature lying about 60° C. above the dew point temperature $T_P$.

At the start of the soiling compensation cycle for example a heating of the sensor to a maximum temperature of 120° C. is effected. The heating continues until the sensor capacitance $C_F$ remains stable, this being the case when the sensor has given off all the moisture This enables the dry capacitance $C_0$ to be determined. In the example illustrated the soiling is so intense that the evaporation of the water is not completely achieved until a sensor temperature of 120° C. is reached. The sensor capacitance $C_F$ has then dropped to the dry capacitance $C_0=8.9$ pF.

Following this heating period of the sensor and starting from the highest temperature reached, cooling is carried out with maximum cooling power until a first rise of the sensor capacitance $C_F$ is to be observed. In the example illustrated this first rise occurs when the sensor temperature has dropped to only about 115° C.

From this instant onwards a slower gradated lowering of the sensor temperature takes place. As a result a gradated rise is imposed on the correspondingly rising sensor capacitance $C_F$. As has been explained with the aid of FIG. 8, this soiling-induced periodic time variation of the sensor capacitance occurs only as long as the sensor temperature lies above the dew point. As soon as the temperature drops below the dew point temperature $T_P$ the periodic time variation gives way to a sudden and then gradual increase of the sensor capacitance. The sensor temperature at this transition is the dew point temperature $T_P$ and the sensor capacitance $C_F$ measured at this temperature is the dew point capacitance value $C_1$ which is stored as new capacitance reference or desired value. In the example illustrated a capacitance desired value $C_1=21.8$ pF is found.

From the diagram of FIG. 9 the characteristic curve of the soiled sensor selected as example can be derived, i.e. the dependence of the sensor capacitance on the sensor temperature, and is plotted in FIG. 10. It is clear from this characteristic curve that with the method described for soiling compensation the soiling-induced rise of the sensor capacitance $C_F$ is ignored by the choice of $C_1$. This method also results in the desired value $C_1$ coming to lie exactly at the base point of the steep characteristic portion and not substantially higher. This is advantageous both for the dynamics of the system, which becomes increasingly sluggish with increasing thickness of the condensation, and for the self-optimization of the control described.

The display of the sensor temperature $T_A$ is kept constant during the entire soiling compensation cycle and reactivated only after the end of the cycle, the display then going exponentially to the new dew point temperature.

For the execution of the method described for automatic soiling compensation it is important to select correctly the rate of the gradated lowering of the sensor temperature.

An advantageous step ensures that the lowering rate sets itself in optimum manner.

As already mentioned, after completion of the heat drying phase of the Peltier element 14 the latter is firstly operated with maximum cooling current until a rise of the sensor capacitance $C_F$ is detected for the first time.

A gradated reduction of the sensor temperature is then effected. Firstly, the sensor temperature (by reducing the desired value $T_S$ of the temperature control) is decreased by 1° C. and then kept at the new temperature value until the sensor capacitance $C_F$ reaches a saturation state, which is characteristic of a soiling-induced increase of the sensor capacitance. Thereafter a reduction of the sensor temperature is made again and so on.

In this manner the gradation frequency and thus the mean lowering rate adapt themselves automatically to the particular conditions obtaining so that the periodic time variations of the $C_F$ value can be satisfactorily detected as response and evaluated.

If the sensor capacitane does not reach a saturation state but permanently rises this is a sign that the sensor temperature has dropped below the dew point. The new desired value $C_1$ is then determined from the last values of the sensor capacitance $C_F$ reached.

The diagram of FIG. 11 shows an enlarged fragment of the temperature curve of FIG. 9 which more clearly illustrates the gradated lowering of the sensor temperature and the diagram B of FIG. 11 shows the corresponding periodic time variations of the sensor capacitance $C_F$. It is also shown in FIG. 11 how the time constant $T_{z1}$ can be determined from the profile of the temperature curve in the soiling cycle.

The periodic time variations of the sensor capacitance $C_F$ can also be generated in a manner other than gradated reduction of the sensor temperature $T_F$. For example, the sensor temperature $T_F$ can be alternately decremented by 2° C. and then again incremented by 1° C. so that a temperature oscillation is superimposed on the declining temperature curve. A corresponding oscillation giving the periodic time variation is then superimposed on the rise of the sensor capacitance in the region above the dew point temperature.

If the sensor is not soiled, no periodic time variations of $C_F$ occur and the first rise of the sensor capacitance does not take place until the dew point is reached, whereupon the first use corresponds to the permanent rise without saturation. In this case the desired value $C_1$ is set to a value which is greater by a predetermined amount that the dry capacitance $C_0$, for example $$C_1 = C_0 + 0.2 \text{ pF}.$$

Finally, at the end of the soiling compensation cycle provisional rough values for the control parameters $K_i$, $K_p$ and $K_d$ are fixed on the basis of the capacitance and temperature changes observed during the cycles. These rough control parameters are then used for the start of the normal control of the moisture-dependent electrical quantity which will however in the normal case still execute oscillations because the control parameters found are adapted only very roughly to the system. With the aid of the previously described oscillation analysis and self-optimizing the system then however determines the exact control parameters from the rough values for $K_p$, $K_i$, $K_d$ and the parameters $P_{2R}$, $P_{2J}$ of the capacitance oscillations.

As mentioned, the soiling compensation cycle described is carried out on each starting-up of the apparatus and possibly repeated at relatively long intervals of time.

We claim:

1. Method for measuring the water vapour dew point in gases in which a moisture-dependent electrical quantity used for indicating the formation of dew droplets on a sensor surface is held by controlling the temperature of the sensor surface at a desired value associated with a stable dew mass and the temperature of the sensor surface is measured, characterized in that for setting the desired value the temperature of the sensor surface is lowered from a value lying above the dew point temperature and a periodic time temperature variation is superimposed on the lowering, and that on simultaneous occurrence of periodic time variations of the moisture-dependent electrical quantity the value of the moisture-dependent electrical quantity measured on the change of the periodic time variations to a monotonic variation is used as the desired value.

2. Method according to claim 1, characterized in that the temperature of the sensor surface is decreased stepwise by a predetermined amount and the periodic time variation of the moisture-dependent electrical quantity is monitored until monotonic increase of said quantity.

3. Method according to claim 2, characterized in that the gradated variations of the temperature of the sensor surface are initiated in dependence upon the variations of the moisture-dependent electrical quantity.

4. Method according to claim 1, characterized in that the sensor surface is first heated to a temperature lying above the dew point of the gas until the moisture-dependent electrical quantity has assumed a stable value, that the stable value is measured as dry value, that then the temperature of the sensor surface is lowered stepwise and that the superimposing of the periodic time temperature variations is started when the first variation of the moisture-dependent electrical quantity is observed.

5. Method according to claim 1, characterized in that the moisture-dependent electrical quantity is a capacitance.

6. Method according to claim 1, characterized in that the control parameters for the control of the moisture-dependent quantity are continuously corrected on the basis of an analysis of oscillations of the moisture-dependent electrical quantity or of the sensor temperature.

7. Method according to claim 6, characterized in that by the oscillation analysis the oscillation amplitudes at two consecutive oscillation maxima and the time interval between said oscillation maxima are determined.

8. Method according to claim 7, characterized in that to detect the oscillation maxima the signs of the slopes of a plurality of consecutive curve portions of the profile of the moisture-dependent electrical quantity or of the sensor temperature are evaluated.

9. Method according to claim 8, characterized in that a sign change between two curve portions indicating a possible oscillation maximum is stored and that on an immediately following new sign change the storing is cancelled whereas when a new sign change does not occur the oscillation maximum is confirmed.

10. Method according to claim 9, characterized in that for storing the sign change a count variable is altered by a predetermined amount and that for confirming the oscillation maximum the count variable is again altered by the same amount in the same direction.

11. Method according to claim 6, characterized in that the control of the moisture-dependent electrical quantity is a proportional-plus-integral-plus-derivative control.

12. Method according to claim 11, characterized in that by the control of the moisture-dependent electrical quantity as controlled variable a temperature desired value is generated and that the temperature desired value is used as command variable for a temperature control which follows in cascade and the controlled variable of which is the temperature of the sensor surface.

13. Method according to claim 12, characterized in that the temperature control following in cascade is a control with fixedly set control parameters.

14. Arrangement for measuring the water vapour dew point in gases including a dew point sensor comprising an electrical sensor element which comprises a sensor surface and which furnishes an electrical signal dependent on the moisture-dependent electrical quantity, an electrical heating and cooling means influencing the temperature of the sensor surface and an electrical temperature sensor furnishing an electrical signal dependent on the temperature of the sensor surface, and a control arrangement which is connected to the dew point sensor and receives the moisture-dependent electrical quantity as controlled variable and supplies to the electrical heating and cooling means a correcting variable by which the moisture-dependent electrical signal is held at a desired value, characterized in that the control arrangement includes a master controller and a follow-up controller which are arranged in cascade, that the master controller receives the moisture-dependent electrical signal as controlled variable and the desired value of the moisture-dependent electrical signal as command variable and emits a temperature desired value signal and that the follow-up controller receives the temperature desired value signal furnished by the master controller as command variable and the temperature-dependent signal furnished by the temperature sensor as controlled variable and supplies the correcting variable to the electrical heating and cooling means.

15. Arrangement according to claim 14, characterized in that the master controller is a proportional-plus-integral-plus-derivative controller, the control parameters of which are corrected on the basis of the oscillation analysis, and that the follow-up controller is a controller with fixedly set control parameters.

16. Arrangement according to claim 14, characterized in that the master controller and the follow-up controller are formed by a microcomputer which also effects the setting of the desired value of the moisture-dependent electrical quantity as well as the oscillation analysis and the correction of the control parameters.

* * * * *